(12) United States Patent
Kang et al.

(10) Patent No.: US 10,588,676 B2
(45) Date of Patent: Mar. 17, 2020

(54) BONE FUSION DEVICE

(71) Applicant: L&K Biomed Co., Ltd., Yongin-si, Gyeonggi-do (KR)

(72) Inventors: Gook-Jin Kang, Seoul (KR); Sunny Kim, Edina, MN (US)

(73) Assignee: L&K Biomed Co., Ltd., Yongin-si, Gyeonggi-do (KR)

( * ) Notice: Subject to any disclaimer, the term of this patent is extended or adjusted under 35 U.S.C. 154(b) by 233 days.

(21) Appl. No.: 15/546,537

(22) PCT Filed: Jan. 27, 2016

(86) PCT No.: PCT/KR2016/000885
§ 371 (c)(1),
(2) Date: Jul. 26, 2017

(87) PCT Pub. No.: WO2016/122208
PCT Pub. Date: Aug. 4, 2016

(65) Prior Publication Data
US 2018/0028246 A1 Feb. 1, 2018

(30) Foreign Application Priority Data
Jan. 30, 2015 (KR) .................. 10-2015-0015161

(51) Int. Cl.
*A61B 17/86* (2006.01)
*A61B 17/70* (2006.01)
*A61B 17/80* (2006.01)

(52) U.S. Cl.
CPC ...... *A61B 17/8685* (2013.01); *A61B 17/7055* (2013.01); *A61B 17/809* (2013.01);
(Continued)

(58) Field of Classification Search
CPC .... A61B 17/844; A61B 17/84; A61B 17/8685
See application file for complete search history.

(56) References Cited

U.S. PATENT DOCUMENTS

| 5,772,662 A | 6/1998 | Chapman et al. |
| 2011/0144702 A1 | 6/2011 | Leroux et al. |
| 2014/0031934 A1* | 1/2014 | Trieu .................. A61F 2/30988 623/17.11 |

FOREIGN PATENT DOCUMENTS

| EP | 0194409 A2 | 9/1986 |
| KR | 10-1999-0077375 A | 10/1999 |

(Continued)

OTHER PUBLICATIONS

English translation of International Search Report and Written Opinion for PCT/KR2016/000885, dated Jun. 22, 2016.
Machine translation of KR 10-1999-0077375, 9 pages.

*Primary Examiner* — Christian A Sevilla
(74) *Attorney, Agent, or Firm* — Medler Ferro Woodhouse Mills PLLC

(57) ABSTRACT

The present invention provides a bone fusion device which allows a distant bone body in a surgery direction to be pulled toward an adjacent bone body in the surgery direction while fusing the adjacent bone bodies. The bone fusion device includes a bone screw which includes a shank having an elongated shape with a circular cross-section, a screw thread formed on one end portion of the shank, and an adjustment female thread formed in the other end portion of the shank; a washer which includes a through hole into which the other end portion of the shank is inserted, and has a cross-sectional area larger than that of the bone screw; and an adjustment screw having an adjustment male thread screwed with the adjustment female thread of the bone screw through a through hole of the washer.

12 Claims, 7 Drawing Sheets

(52) U.S. Cl.
    CPC ...... *A61B 17/8042* (2013.01); *A61B 17/8047* (2013.01); *A61B 17/863* (2013.01); *A61B 17/8605* (2013.01); *A61B 17/8695* (2013.01); *A61B 2017/8655* (2013.01)

(56)         References Cited

FOREIGN PATENT DOCUMENTS

| KR | 10-2007-0009589 A | 1/2007 |
| KR | 10-2013-0007333 A | 1/2013 |
| KR | 10-2015-0024238 A | 3/2015 |

\* cited by examiner

BONE FUSION DEVICE

CROSS-REFERENCE TO RELATED APPLICATIONS

This application claims priority to Korean Patent Application No. 10-2015-0015161 filed on Jan. 30, 2015 in the Korean Intellectual Property Office, and International Application No. PCT/KR2016/000885, filed on Jan. 27, 2016, the entire disclosures of which are incorporated herein by reference.

FIELD OF THE INVENTION

The present invention relates to a bone fusion device, and more specifically, to a bone fusion device which allows a distant bone body in a surgery direction to be pulled toward an adjacent bone body in the surgery direction while fusing the adjacent bone bodies.

BACKGROUND OF THE INVENTION

Conventional lumbar fusion surgery may result in excessive displacement at adjacent segments other than a surgical site after the operation, resulting in secondary lesions at the adjacent segments during a long-term use and reoperation is often required. In particular, when a problem occurs in a joint between a sacrum (sacral vertebrae) and an ilium (pelvis), a sacroiliac joint syndrome may develop. This syndrome is accompanied by lumbar pain, leading to pain in the thighs and below the hips, and sometimes pain along a sciatic nerve occurs. Further, in a severe case, it has been reported that it becomes difficult to sit.

For the purpose of treating such pains, a sacroiliac (SI) joint fusion implant is used. However, since the sacrum and the ilium are simply fixed using a screw during the operation, loosening occurs at the joint site after a long period of time, and therefore, there is a problem that the reoperation should be performed.

In a method disclosed in Korean Patent Laid-Open Publication No. 10-1999-0077375 developed later, a washer and a bone screw are used by differently forming a diameter of a thread to be transplanted to the segmented bone. However, if rotating the screw until it comes into contact with the washer, the screw may penetrate the bone body located at a region far from the washer of the bone body to be fused, thereby damaging other tissues of a human body. In addition, if tightening the screw only to a position in which the screw does not penetrate the bone body located at the region far from the washer by using an observation equipment, the bone bodies to be fused cannot be sufficiently adhered to each other. Therefore, a length of the screw should be formed within a range so that the bone body to be fused is brought into contact with the washer accurately while fusing the bone bodies to be fused. Accordingly, screws having a required length should be prepared based on differences in the bone structure of each patient, and thus the efficacy of this treatment may be uncertain.

REFERENCES

Korean Patent Laid-Open Publication No. 10-1999-0077375.

SUMMARY OF THE INVENTION

In consideration of the above-mentioned circumstances, it is an object of the present invention to provide a bone fusion device which allows a distant bone body in a surgery direction to be pulled toward an adjacent bone body in the surgery direction while fusing the adjacent bone bodies, so as to safely perform the bone fusion surgery.

In order to accomplish the above-described object, there is provided a bone fusion device including: a bone screw which includes a shank having an elongated shape with a circular cross-section, a screw thread formed on one end portion of the shank, and an adjustment female thread formed in the other end portion of the shank; a washer which includes a through hole into which the other end portion of the shank is inserted, and has a cross-sectional area larger than that of the bone screw; and an adjustment screw having an adjustment male thread screwed with the adjustment female thread of the bone screw through a through hole of the washer.

The washer may include a washer tube having a through hole formed therein, and a flange part integrally formed with the washer tube and having a cross-sectional area larger than that of the washer tube.

In addition, the flange part may have washer wedges protruding therefrom to the washer tube.

Further, the washer tube may include a washer thread or washer wedges formed on an outer circumference thereof.

Further, the washer tube may have an outer diameter gradually increased toward the flange part.

Further, the flange part may have one or more pinholes formed therein, and fixing pins are inserted into the pinholes.

Further, the washer may have a head seat formed in one side thereof on which the head of the adjustment screw is seated, and the head seat and a lower surface of the head of the adjustment screw abutting the head seat respectively have an anti-rotation means formed thereon.

Further, the anti-rotation means may be angular teeth formed radially on the head seat and the lower surface of the head, respectively.

Further, the shank may have a wrench groove formed therein at a position deeper than the adjustment female thread.

Further, the shank may have a rotation drive groove formed in the other end portion thereof, or a rotation drive surface formed on an outer circumference thereof.

Further, the washer may have a locking means installed therein to prevent the adjustment screw from being loosened.

Furthermore, the locking means may be a rotation cover which is rotatably installed in the washer to prevent the adjustment screw from being loosened by partially covering the adjustment screw.

Furthermore, the locking means may include one or more head cutting faces formed on an outer circumference of the head of the adjustment screw, and a rotation cam having a rotatable cam radius, and the rotation cam has one or more cam cutting faces that are formed by cutting off to selectively allow the adjustment screw to be freely rotated.

Advantageous Effects

According to the present invention, it is possible to safely perform the bone fusion surgery by pulling the distant bone body in a surgery direction toward the adjacent bone body in the surgery direction while fusing the adjacent bone bodies. In particular, it is possible to prevent other tissues from being damaged by the screw while performing the bone fusion surgery.

In addition, an operator may adjust an amount of pulling of the screw as necessary while performing the bone fusion surgery.

DETAILED DESCRIPTION

Figure 1:
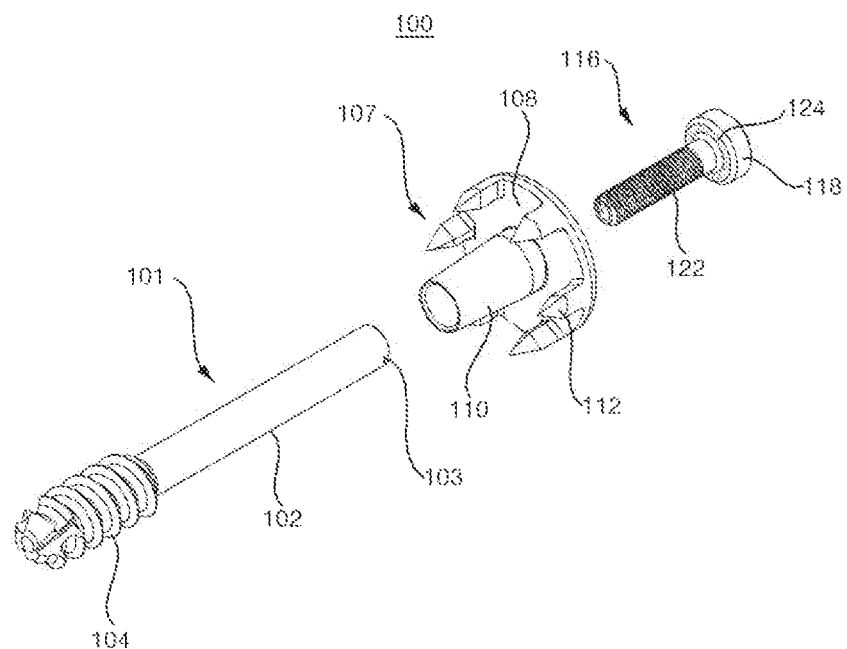
FIG. 1 is an exploded perspective view illustrating a bone fusion device according to Embodiment 1 of the present invention.

Hereinafter, preferable embodiments of the present invention will be described with reference to the accompanying drawings. Referring to the drawings, wherein like reference characters designate like or corresponding parts throughout the several views. In the embodiments of the present invention, a detailed description of publicly known functions and configurations that are judged to be able to make the purport of the present invention unnecessarily obscure will not be described.

Figure 2:
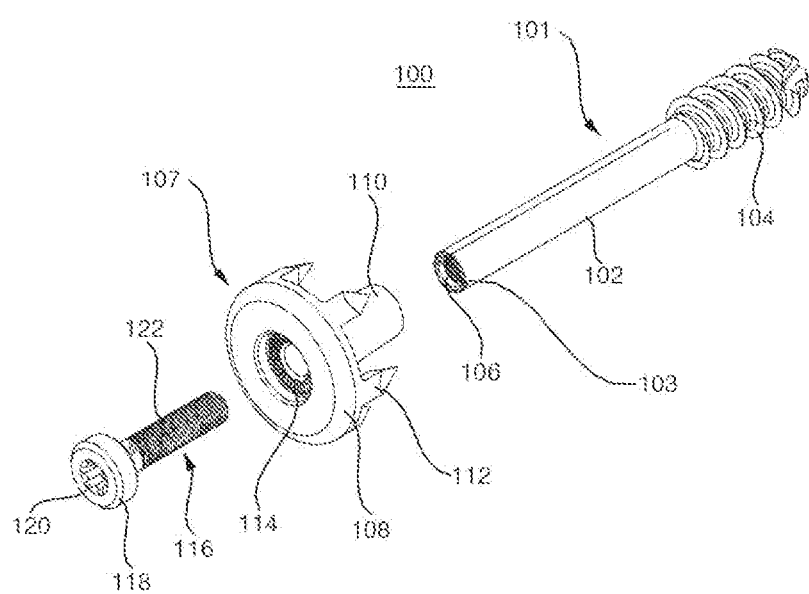
FIG. 2 is an exploded perspective view illustrating the bone fusion device of FIG. 1 as viewed from a different direction.

FIGS. 1 and 2 illustrate a bone fusion device 100 according to Embodiment 1 of the present invention. The bone fusion device 100 generally includes a bone screw 101 inserted into bone bodies, a washer 107 into which the bone screw 101 is inserted and supported by the bone body, and an adjustment screw 116 screwed with the bone screw 101 to adjust an interval between the washer 107 and the bone screw 101. The bone fusion device 100 may be made of metal or an alloy, and for example, titanium, which is harmless to the human body, may be used.

The bone screw 101 includes a shank 102 having an elongated shape with a circular cross-section, a screw thread 104 formed on one end portion of the shank 102, and an adjustment female thread 106 formed in the other end portion of the shank 102.

The shank 102 with a smooth surface has a structure for facilitating an insertion thereof into the washer 107, as well as preventing an interference with the bone body, when the bone screw 101 is pulled toward the washer 107 by the adjustment screw 116.

The screw thread 104 is formed on one end portion of the shank 102 and has an outer diameter larger than that of the shank 102. The adjustment female thread 106 formed in the other end portion of the shank 102 is screwed with the adjustment screw 116.

In order to insert the bone screw 101 into the bone bodies, a rotational force should be transmitted thereto. For this purpose, in Embodiment 1 of the present invention, the shank 102 has a screw-wrench groove 105 formed therein at a position deeper than the adjustment female thread 106. Therefore, a wrench (not illustrated) having a diameter smaller than that of the adjustment female thread 106 may be fitted to the screw-wrench groove 105 to rotate the bone screw 101. Further, a rotation drive groove 103 may be formed in the other end portion of the shank 102. The rotation drive groove 103 may have grooves having various shapes such as a straight-line shape, or a cross shape depending on the shape of a tool to be inserted. Therefore, it is also possible to rotate the shank by inserting a tool such as a type of driver into the rotation drive groove 103 from an outside of the shank 102.

The washer 107 includes a through hole into which the other end portion of the shank 102 is inserted and should have a cross-sectional area larger than that of the bone screw so as to be supported by the bone bodies. For this purpose, the washer 107 includes a washer tube 110 having a through hole formed therein, and a flange part 108 formed integrally with the washer tube 110 and having a cross-sectional area larger than that of the washer tube 110. The flange part 108 includes washer wedges 112 protruding therefrom to the washer tube 110 so that the flange part 108 is stably fixed to the bone body.

A plurality of washer wedges 112 may be formed on the flange part 108 in a circumferential direction.

The adjustment screw 116 has an adjustment male thread 122 and a head 118. The head 118 has a head-wrench groove 120 formed therein to transmit a rotational force of a tool to the adjustment screw 116.

The washer 107 has a head seat formed in one side thereof on which the head 118 of the adjustment screw 116 is seated. The head seat and a lower surface of the head of the adjustment screw 116 abutting the head seat respectively have an anti-rotation means formed thereon.

As the anti-rotation means, for example, angular teeth 114 and 124 formed radially on the head seat and the lower surface of the head 118, respectively, may be used, and other techniques known in the art may also be used. In particular, by forming the cross-sections of the angular teeth 114 and 124 in a tight-angled triangle, rotation of the adjustment screw 116 in one direction is allowed, while rotation thereof in an opposite direction is prevented. Therefore, after the adjustment screw 116 is tightened, the adjustment screw 116 and the washer 107 may be maintained in a locked state.

The bone fusion device 100 according to Embodiment 1 of the present invention is basically configured as described above. Hereinafter, a process of performing the operation using the bone fusion device 100 will be described with reference to FIGS. 3 and 4.

First, the bone screw 101 is inserted into two bone bodies to be fused. Herein, the ilium 10 and the sacrum 12 will be described as an example. Guide holes (not illustrated) may be formed in the sacrum and the ilium by a screw (not illustrated) having a diameter smaller than that of the bone screw 101 before inserting the bone screw 101, thus to easily insert the bone screw 101 into the guide holes. The bone screw 101 is inserted from the sacrum 12 toward the ilium 10. The reason is that, if the operation is performed on the ilium 10 side, the surrounding soft tissues of the human body may be easily damaged. Of course, the present invention is not limited to the case in which the operation is performed from the ilium 10 toward the sacrum 12 as described above.

Figure 3:
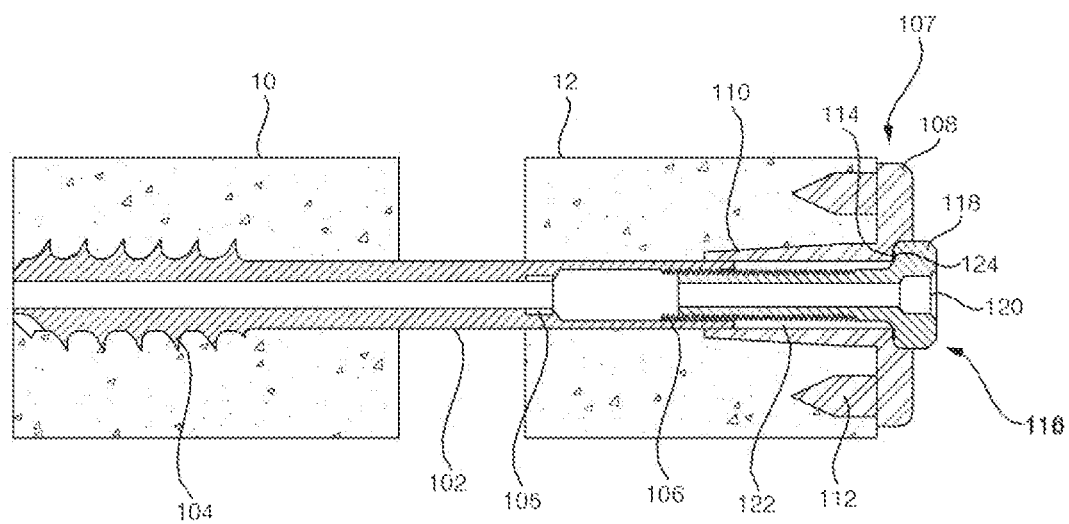
FIGS. 3 and 4 are cross-sectional views illustrating a process of performing a bone fusion surgery using the bone fusion device of FIG. 1.

Then, the shank 102 of the bone screw 101 is inserted into the washer tube 110 of the washer 107 so that the washer 107 comes into close contact with the sacrum 12 while rotating the same. At this time, the washer wedges 112 of the washer 107 are stuck in the sacrum 12, and the rotation of the washer 107 with respect to the sacrum 12 is blocked. Next, the adjustment screw 116 is screwed to the adjustment female thread 106 of the bone screw 101 through the washer 107. This state is illustrated in FIG. 3.

Figure 4:
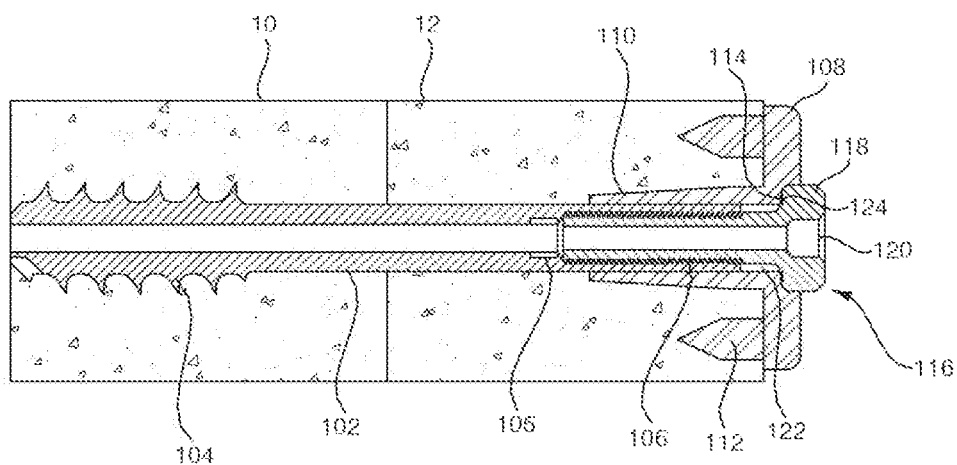

When continuously rotating the adjustment screw 116, since the washer 107 is fixed to the sacrum 12, the bone screw 101 is pulled toward the washer. As a result, the ilium 10 and the sacrum 12 are fused as illustrated in FIG. 4 while the ilium 10 with the bone screw 101 screwed thereto is pulled together. The rotation of the bone screw 101 is prevented even if rotating the adjustment screw 116, such that there is no risk of damaging the tissues positioned at an outside of the ilium 10 due to penetration of the ilium 10 by the bone screw 101. In addition, since an amount of pulling of the bone screw 101 can be adjusted according to an amount of rotation of the adjustment screw 116, the operator may flexibly perform the operation depending on the patient's condition during the surgical procedure.

Figure 5:
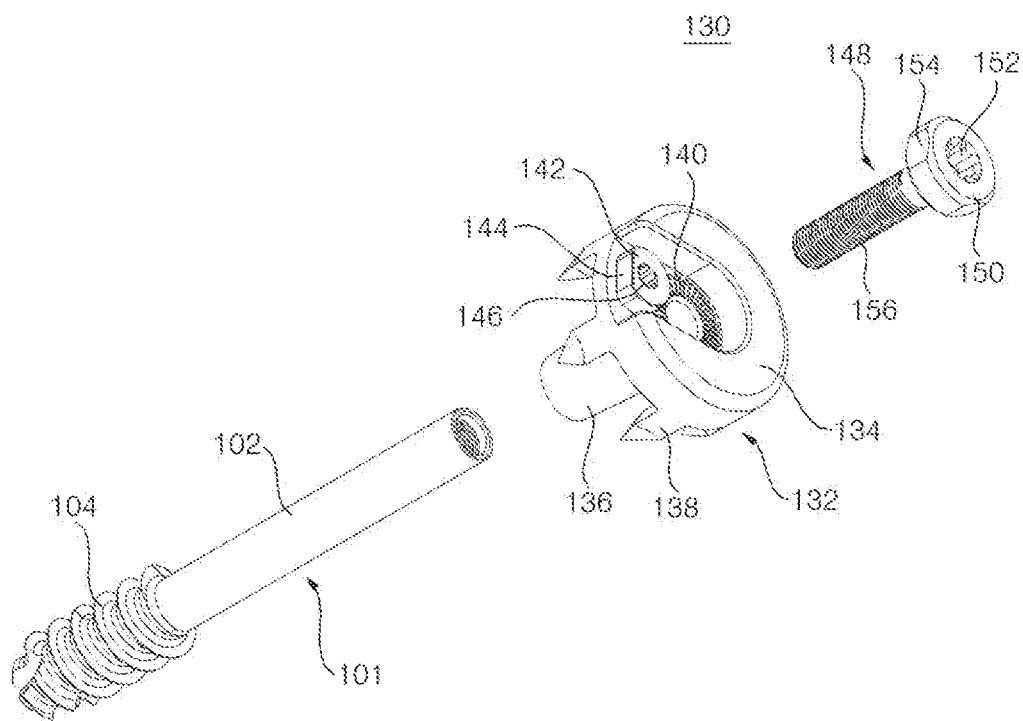
FIG. 5 is an exploded perspective view illustrating a bone fusion device according to Embodiment 2 of the present invention.

Next, a bone fusion device 130 according to Embodiment 2 of the present invention will be described with reference to FIGS. 5 and 6. Unlike the bone fusion device 100 of Embodiment 1, the bone fusion device 130 has a locking means installed in a washer 132 to prevent the adjustment screw 148 from being loosened.

The bone fusion device 130 generally includes a bone screw 101 inserted into bone bodies, a washer 132 into which the bone screw 101 is inserted and supported by the bone body, and an adjustment screw 148 screwed with the bone screw 101 to adjust an interval between the washer 132 and the bone screw 101. The bone fusion device 130 may be made of metal or an alloy, and for example, titanium, which is harmless to the human body, may be used.

The bone screw 101 has the same configuration as Embodiment 1, therefore will not be described in detail.

The washer 132 includes a through hole into which the other end portion of the shank 102 is inserted and should have a cross-sectional area larger than that of the bone screw so as to be supported by the bone bodies. For this purpose, the washer 132 includes a washer tube 136 formed with the through hole and a flange part 134 formed integrally with the washer tube 136 and having a cross-sectional area larger than that of the washer tube 136. The flange part 134 includes washer wedges 138 protruding therefrom to the washer tube 136 so that the flange part 134 is stably fixed to the bone body.

A plurality of washer wedges 138 may be formed on the flange part 134 in the circumferential direction.

The adjustment screw 148 has an adjustment male thread 156 and a head 150. The head 150 has a head-wrench groove 152 formed therein to transmit a rotational force of a tool to the adjustment screw 148.

The washer 132 has a head seat formed in one side thereof on which the head 150 of the adjustment screw 148 is seated. The head seat and a lower surface of the head of the adjustment screw 148 abutting the head seat respectively have an anti-rotation means formed thereon.

As the anti-rotation means, angular teeth 140 formed radially on the head seat and the lower surface of the head 150 may be used, or other techniques known in the art may also be used. In particular, by forming the cross section of the angular teeth 140 in a right-angled triangle, rotation of the adjustment screw 148 in one direction is allowed, while rotation thereof in an opposite direction is prevented. After the adjustment screw 148 is tightened, the adjustment screw 148 and the washer 132 may be maintained in a locked state.

The locking means includes one or more head cutting faces 154 formed on an outer circumference of the head 150 of the adjustment screw 148, and a rotation cam 142 having a rotatable cam radius. The rotation cam 142 has one or more cam cutting faces 144 that are formed by cutting off to selectively allow the adjustment screw 148 to be freely rotated.

In addition, the rotation cam 142 may have a cam-wrench groove 146 formed therein, thereby rotating the rotation cam 142 by inserting a tool such as a wrench into the cam-wrench groove.

Figure 6:
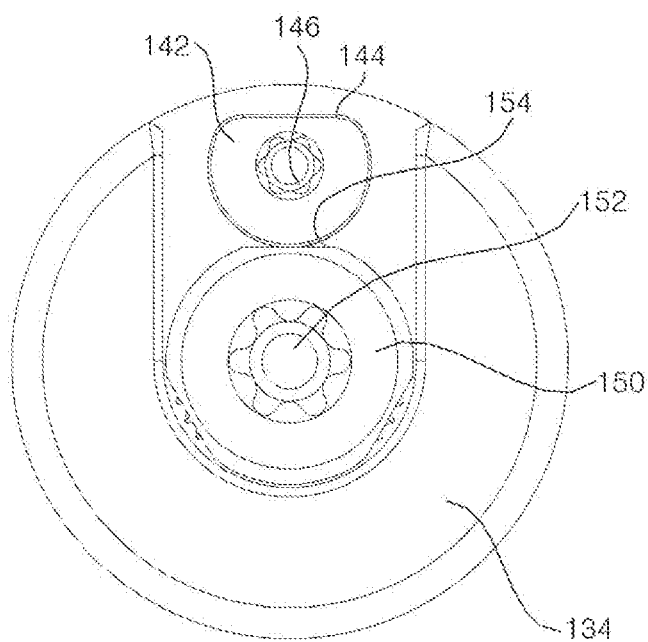
FIG. 6 is a side view illustrating the bone fusion device of FIG. 5.

Accordingly, as illustrated in FIG. 6, when the outer circumference of the cam-wrench groove 146 having the rotatable cam radius comes in contact with the head cutting face 154 of the adjustment screw 148, the rotation cam 142 is not rotated, and in this state, the rotation of the adjustment screw 148 is blocked. When tightening the adjustment screw 148, the rotation cam 142 is rotated so that the cam cutting face 144 faces the adjustment screw 148, and in this state, the adjustment screw may be freely rotated.

Figure 7:
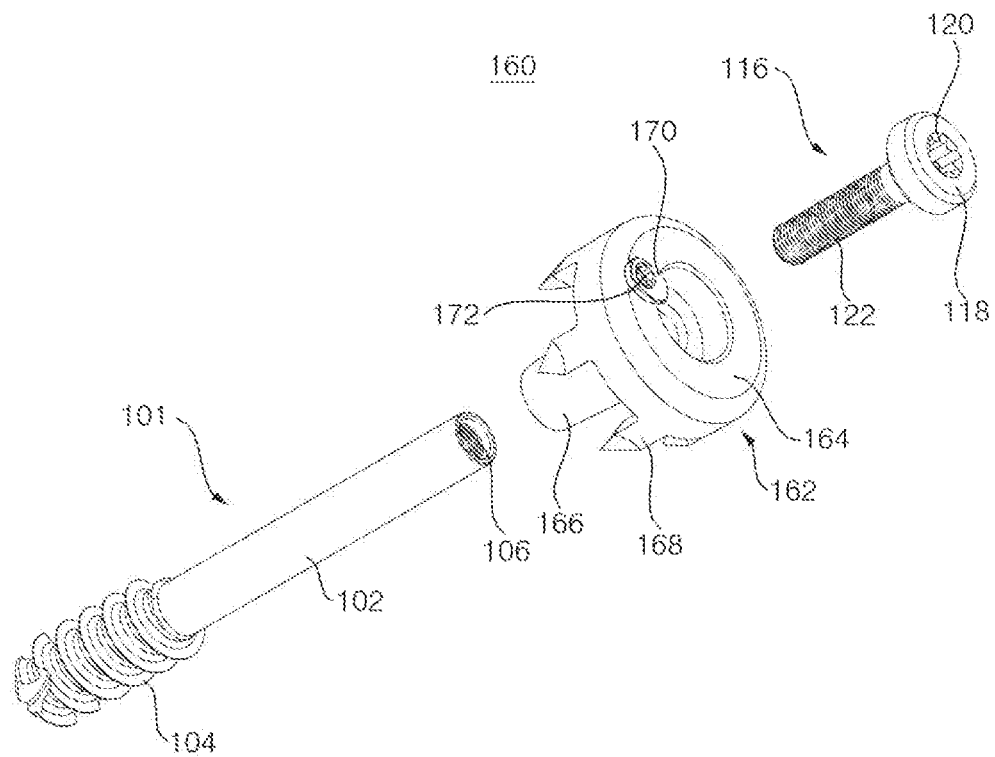
FIG. 7 is an exploded perspective view illustrating a bone fusion device according to Embodiment 3 of the present invention.

Next, a bone fusion device 160 according to Embodiment 3 of the present invention will be described with reference to FIGS. 7 and 8. This embodiment discloses the bone fusion device 160 having a locking means of a different type from Embodiment 2.

The bone fusion device 160 generally includes a bone screw 101 inserted into bone bodies, a washer 162 into which the bone screw 101 is inserted and supported by the bone body, and an adjustment screw 116 screwed with the bone screw 101 to adjust an interval between the washer 162 and the bone screw 101. The bone fusion device 160 may be made of metal or an alloy, and for example, titanium, which is harmless to the human body, may be used.

The bone screw 101 and the adjustment screw 116 have the same configuration as those of Embodiment 1, therefore will not be described in detail.

The washer 162 includes a through hole into which the other end portion of the shank 102 is inserted and should have a cross-sectional area larger than that of the bone screw so as to be supported by the bone bodies. For this purpose, the washer 162 includes a washer tube 166 having a through hole formed therein, and a flange part 164 formed integrally with the washer tube 166 and having a cross-sectional area larger than that of the washer tube 166. The flange part 164 has washer wedges 168 protruding therefrom to the washer tube 166 so that the flange part 164 is stably fixed to the bone body.

A plurality of washer wedges 168 may be formed on the flange part 164 in the circumferential direction.

The locking means is a rotation cover 170 which is rotatably installed in the washer 164 to prevent the adjustment screw 116 from being loosened by partially covering the adjustment screw 116.

The rotation cover 170 should have a shape that covers or does not cover a part of the adjustment screw 116 by rotation, for example, a polygon, an ellipse, a waterdrop, a half moon, a crescent shape or the like.

The rotation cover 170 may have a cover-wrench groove 172 formed therein to insert a tool such as a wrench into the groove so as to rotate the rotation cover 170.

Figure 8:
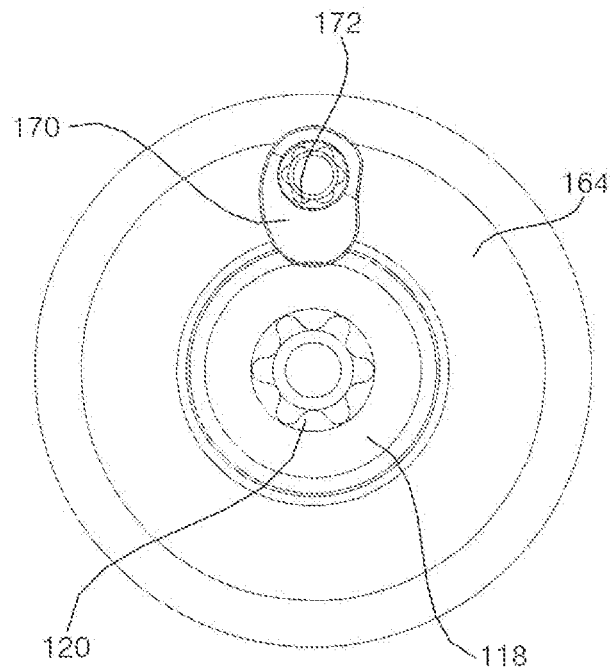
FIG. 8 is a side view illustrating the bone fusion device of FIG. 7.
Figure 9:
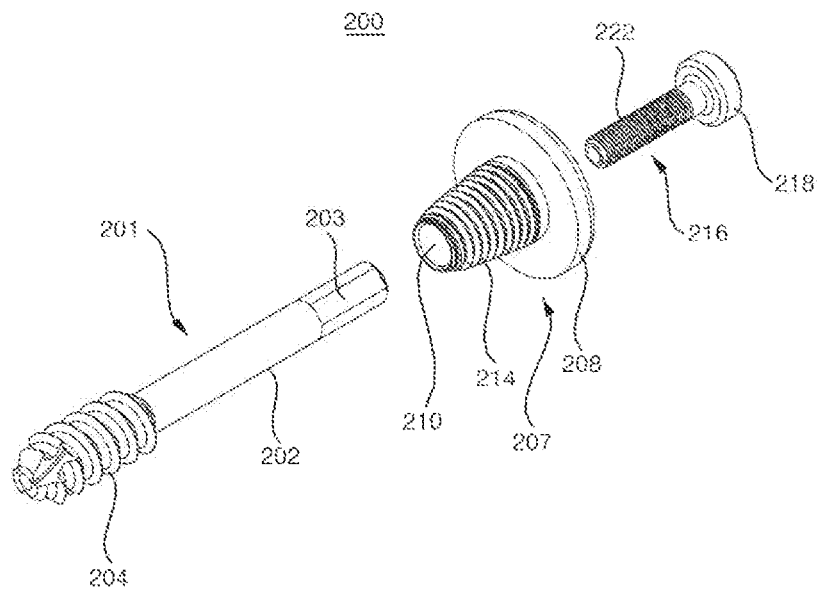
FIG. 9 is an exploded perspective view illustrating a bone fusion device according to Embodiment 4 of the present invention as viewed from one direction.
Figure 10:
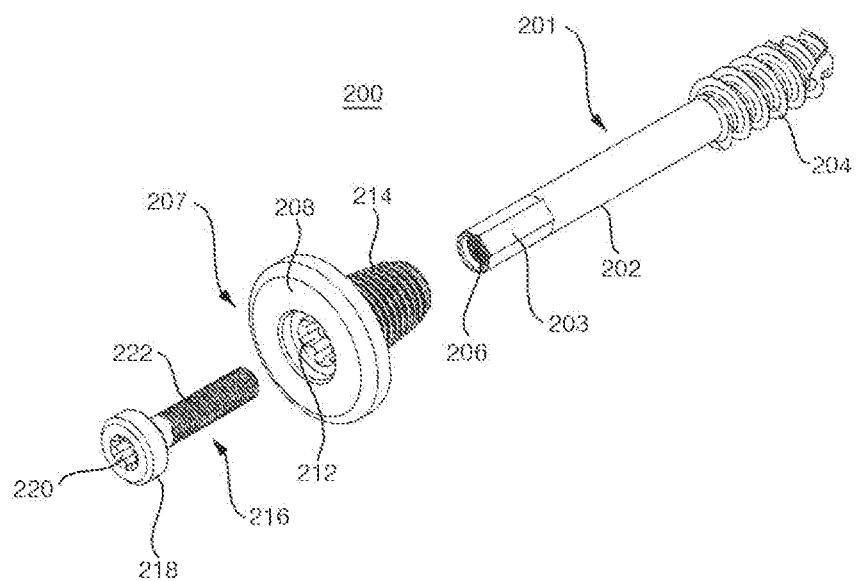
FIG. 10 is an exploded perspective view illustrating the bone fusion device of FIG. 9 as viewed from a different direction.

Accordingly, when the rotation cover 170 is positioned as illustrated in FIG. 8, a part thereof covers a part of the head 118 of the adjustment screw 116, and in this state, the rotation of the adjustment screw 116 is blocked. When rotating the rotation cover 170, the head 118 of the adjustment screw 116 is not covered with the rotation cover 170, and in this state, the adjustment screw may be loosened by rotation.

Next, a bone fusion device 200 according to Embodiment 4 of the present invention will be described with reference to FIGS. 9 to 12. The bone fusion device 200 generally includes a bone screw 201 inserted into bone bodies, a washer 207 inserted into the bone screw 201 and supported by the bone body, and an adjustment screw 216 screwed with the bone screw 201 to adjust an interval between the washer 207 and the bone screw 201. The bone fusion device 200 may be made of metal or an alloy, and for example, titanium, which is harmless to the human body, may be used.

The bone screw 201 includes a shank 202 having an elongated shape with a circular cross-section, a screw thread 204 formed on one end portion of the shank 202, and an adjustment female thread 206 formed in the other end portion of the shank 202.

The shank 202 with a smooth surface has a structure for facilitating an insertion thereof into the washer 207, as well as preventing an interference with the bone body, when the bone screw 201 is pulled toward the washer 207 by the adjustment screw 216.

The screw thread 204 is formed on one end portion of the shank 202 and has an outer diameter larger than that of the shank 202. The adjustment female thread 206 formed in the other end portion of the shank 202 is screwed with the adjustment screw 216.

In order to insert the bone screw 201 into the bone bodies, a rotational force should be transmitted thereto. For this purpose, in Embodiment 4 of the present invention, the shank 202 has a screw-wrench groove 205 formed therein at a position deeper than the adjustment female thread 206. Therefore, a wrench (not illustrated) having a diameter smaller than that of the adjustment female thread 206 may be fitted to the screw-wrench groove 205 to rotate the bone screw 201. In addition, the shank 202 has a rotation drive surface 203 having a polygonal cross-section formed on an outer circumference at the other end portion thereof. Therefore, it is also possible to rotate the bone screw by fitting a female wrench to the rotation drive surface 203 from the outside of the shank 202.

The washer 207 includes a through hole into which the other end portion of the shank 202 is inserted and should have a cross-sectional area larger than that of the bone screw so as to be supported by the bone bodies. For this purpose, the washer 207 includes a washer tube 210 having a through hole formed therein, and a flange part 208 formed integrally therewith and having a cross-sectional area larger than that of the washer tube 210. The washer tube 210 has a washer thread 214 formed on an outer circumference of the washer tube 210 so that the washer 207 is fixed to the bone body. Further, instead of the washer thread 214, washer wedges protruding at a constant interval may be formed on the washer tube 210 in a longitudinal direction thereof. Furthermore, the washer thread 214 may have an outer diameter gradually increased toward the flange part 208 to enlarge a contact area with the bone body, so as to stably support the bone body.

The adjustment screw 216 has an adjustment male thread 222 and a head 218. The head 218 has a head-wrench groove 220 formed therein to transmit a rotational force of a tool to the adjustment screw 216.

The washer 207 may have a head seat formed in one side thereof on which the head 218 of the adjustment screw 216 is seated. A washer-wrench groove 212 for rotating the washer 207 to insert the washer thread 214 into the bone body may be formed in the head seat.

The bone fusion device 200 according to Embodiment 4 of the present invention is basically configured as described above. Hereinafter, a procedure of performing the operation using the bone fusion device 200 will be described with reference to FIGS. 11 and 12.

First, the bone screw 201 is inserted into two bone bodies to be fused. Herein, the ilium 10 and the sacrum 12 will be described as an example. Of course, it is possible to perform the operation from the sacrum 12 toward the ilium 10. Guide holes (not illustrated) may be formed in the sacrum and the ilium by a screw (not illustrated) having a diameter smaller than that of the bone screw 201 before inserting the bone screw 201, thus to easily insert the bone screw 201 into the guide holes. The bone screw 201 is inserted from the sacrum 12 toward the ilium 10. The reason is that, if the operation is performed on the ilium 10 side, the surrounding soft tissues of the human body may be easily damaged.

Figure 11:
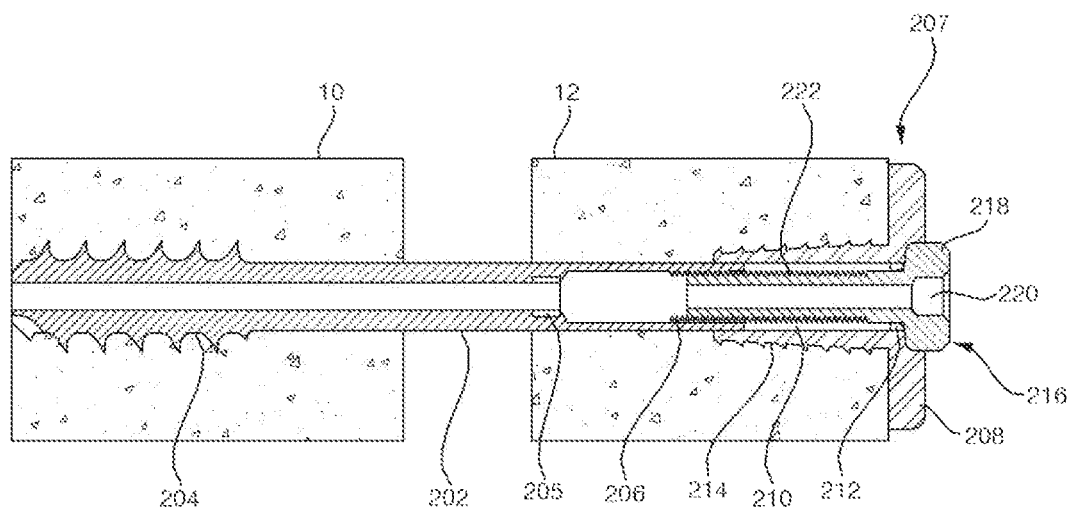
FIGS. 11 and 12 are cross-sectional views illustrating a process of performing a bone fusion surgery using the bone fusion device of FIG. 9.

Then, the shank 202 of the bone screw 201 is inserted into the washer tube 210 of the washer 207 so that the washer 207 comes into close contact with the sacrum 12 while rotating the same. As a result, the washer thread 214 is screwed to the sacrum 12, and the washer 207 is stably fixed to the sacrum 12. Next, the adjustment screw 216 is screwed to the adjustment female thread 206 of the bone screw 201 through the washer 207. This state is illustrated in FIG. 11.

Figure 12:
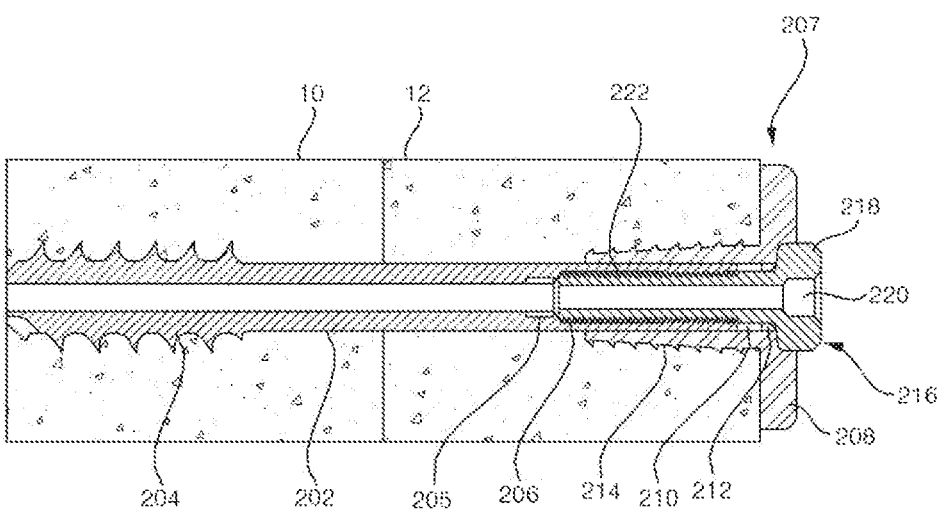

When continuously rotating the adjustment screw 216, since the washer 207 is fixed to the sacrum 12, the bone screw 201 is pulled toward the washer. As a result, the ilium 10 and the sacrum 12 are fused as illustrated in FIG. 12 while the ilium 10 with the bone screw 201 screwed thereto is pulled together. The rotation of the bone screw 201 is prevented even if rotating the adjustment screw 216, such that there is no risk of damaging the tissues positioned at an outside of the ilium 10 due to penetration of the ilium 10 by the bone screw 201. In addition, since an amount of pulling of the bone screw 201 can be adjusted according to an amount of rotation of the adjustment screw 216, the operator may flexibly perform the operation depending on the patient's condition during the surgical procedure.

Figure 13:
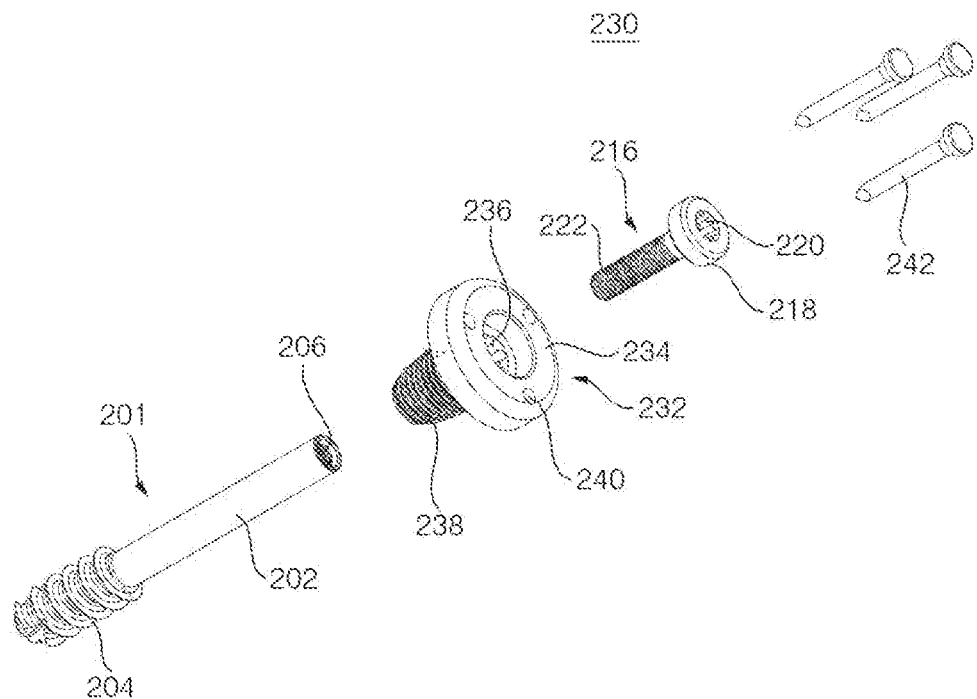
FIG. 13 is an exploded perspective view illustrating a bone fusion device according to Embodiment 5 of the present invention as viewed from one direction.
Figure 14:
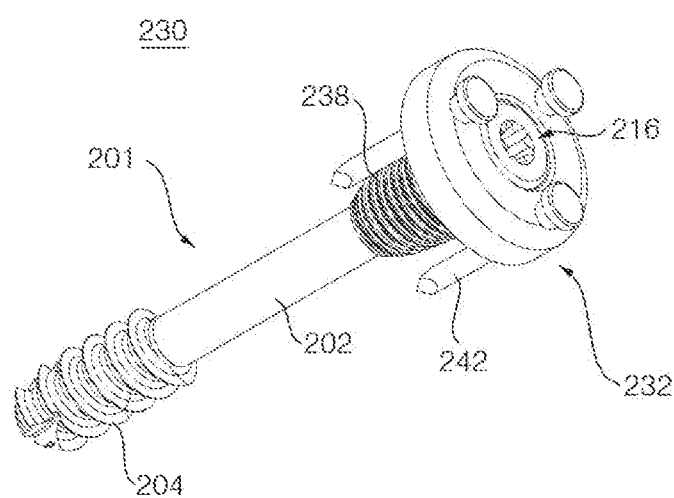
FIG. 14 is an assembled perspective view illustrating the bone fusion device of FIG. 13.

Next, a bone fusion device 230 according to Embodiment 5 of the present invention will be described with reference to FIGS. 13 and 14. The bone fusion device 230 generally includes a bone screw 201 inserted into bone bodies, a washer 232 into which the bone screw 201 is inserted and supported by the bone body, and an adjustment screw 216 screwed with the bone screw 201 to adjust an interval between the washer 232 and the bone screw 201. The bone fusion device 200 may be made of metal or an alloy, and for example, titanium, which is harmless to the human body, may be used.

The bone screw 201 and the adjustment screw 216 have same configuration as those of Embodiment 4, therefore will not be described in detail.

The washer 232 includes a through hole into which the other end portion of the shank 202 is inserted and should have a cross-sectional area larger than that of the bone screw so as to be supported by the bone bodies. For this purpose, the washer 232 includes a washer tube 210 having a through hole formed therein, and a flange part 234 integrally formed with the washer tube 210 and having a cross-sectional area larger than that of the washer tube 210. The washer tube 210 has a washer thread 238 protruding therefrom to the washer tube 210 so that the washer 232 is stably fixed to the bone body. Further, instead of the washer thread 238, washer wedges protruding at a constant interval may be formed on the washer tube 210 in a longitudinal direction thereof. Furthermore, the washer thread 238 may have an outer diameter gradually increased toward the flange part 234 to enlarge a contact area with the bone body, so as to stably support the bone body.

In addition, the washer 232 may have a head seat formed in one side thereof on which the head 218 of the adjustment screw 216 is seated. The head seat may have a washer-wrench groove 236 formed thereon for rotating the washer 232 to insert the washer thread 238 into the bone body.

In addition, the flange part 234 has one or more pinholes 240 formed therein, and fixing pins 242 are inserted into the pinholes 240 to be fixed to the bone body. In Embodiment 5, three fixing pins 242 are arranged at an interval of about 120 degrees. That is, since the washer 232 is fixed to the bone body by screwing, the used fixing pins 242 may prevent the washer from being loosened due to the rotation.

It is also possible to additionally install the locking means in the washer 232 as described in Embodiment 2 or 3.

While the present invention has been described with reference to the preferred embodiments, it will be understood by those skilled in the related art that various modifications and variations may be made therein without departing from the scope of the present invention as defined by the appended claims.

DESCRIPTION OF REFERENCE NUMERALS

10: ilium, 12: sacrum
100, 130, 160, 200, 230: bone fusion device, 101, 201: bone screw
102, 202: shank, 103: rotation drive groove
104, 204: screw thread, 105, 205: screw-wrench groove
106, 206: adjustment female thread 107, 132, 162, 207, 232: washer
108, 134, 164, 208, 234: flange part 110, 136, 166, 210: washer tube
112, 138, 168: washer wedge, 114, 124, 140: angular teeth
116, 148, 216: adjustment screw, 118, 150, 218: head
120, 152, 220: head-wrench groove, 122, 156, 222: adjustment male thread
142: rotation cam, 144: cam cutting face
146: cam-wrench groove, 154: head cutting face
170: rotation cover, 172: cover-wrench groove
203: rotation drive surface, 212, 236: washer-wrench groove
214, 238: washer thread, 240: pin hole
242: fixing pin

The invention claimed is:

1. A bone fusion device comprising:
   a bone screw which includes a shank having an elongated shape with a circular cross-section, a screw thread formed on one end portion of the shank, and an adjustment female thread formed in the other end portion of the shank;
   a washer which includes a through hole into which the other end portion of the shank is inserted, and has a cross-sectional area larger than that of the bone screw; and
   an adjustment screw having an adjustment male thread screwed with the adjustment female thread of the bone screw through a through hole of the washer,
   wherein the washer includes a washer tube having a through hole formed therein, and a flange part integrally formed with the washer tube and having a cross-sectional area larger than that of the washer tube; and
   wherein the washer tube has an outer diameter gradually increased toward the flange part.

2. The bone fusion device according to claim 1, wherein the flange part has washer wedges protruding therefrom to the washer tube.

3. The bone fusion device according to claim 1, wherein the washer tube includes a washer thread or washer wedges formed on an outer circumference thereof.

4. The bone fusion device according to claim 1, wherein the bone fusion device further comprises fixing pins, the flange part has one or more pinholes formed therein, and said fixing pins are inserted into the pinholes.

5. The bone fusion device according to claim 1, wherein the washer has a head seat formed in one side thereof on which a head of the adjustment screw is seated, and
   the head seat and a lower surface of the head of the adjustment screw abutting the head seat respectively have an anti-rotation means formed thereon.

6. The bone fusion device according to claim 5, wherein the anti-rotation means is angular teeth formed radially on the head seat and the lower surface of the head, respectively.

7. The bone fusion device according to claim 1, wherein the shank has a wrench groove formed therein at a position deeper than the adjustment female thread.

8. The bone fusion device according to claim 1, wherein the shank has a rotation drive groove formed in the other end portion thereof.

9. The bone fusion device according to claim 1, wherein the shank has a rotation drive surface formed on an outer circumference thereof.

10. The bone fusion device according to claim 1, wherein the washer has a locking means installed therein to prevent the adjustment screw from being loosened.

11. The bone fusion device according to claim 10, wherein the locking means is a rotation cover which is rotatably installed in the washer to prevent the adjustment screw from being loosened by partially covering the adjustment screw.

12. The bone fusion device according to claim 10, wherein the locking means includes one or more head cutting faces formed on an outer circumference of the head of the adjustment screw, and a rotation cam having a rotatable cam radius, and the rotation cam has one or more cam cutting faces that are formed by cutting off to selectively allow the adjustment screw to be freely rotated.

* * * * *